United States Patent
Hager et al.

(12) 
(10) Patent No.: US 6,663,885 B1
(45) Date of Patent: Dec. 16, 2003

(54) AQUEOUS LIPOSOME SYSTEM AND A METHOD FOR THE PREPARATION OF SUCH A LIPOSOME SYSTEM

(75) Inventors: Jörg-Christian Hager, Cologne (DE); Josef-Peter Löhr, Hilden (DE); Manfred Dürr, Bergheim-Glessen (DE)

(73) Assignee: A. Natterman & Cie GmbH, Cologne (DE)

( * ) Notice: Subject to any disclaimer, the term of this patent is extended or adjusted under 35 U.S.C. 154(b) by 2059 days.

(21) Appl. No.: 08/612,074

(22) Filed: Mar. 7, 1996

Related U.S. Application Data

(63) Continuation of application No. 08/459,291, filed on Jun. 2, 1995, now abandoned, which is a continuation-in-part of application No. 08/205,520, filed on Mar. 3, 1994, now abandoned.

(30) Foreign Application Priority Data

Mar. 15, 1995 (DE) .......................... 43 08 121

(51) Int. Cl.[7] .............................................. A61K 9/127
(52) U.S. Cl. ...................................................... 424/450
(58) Field of Search ................................ 424/450, 1.21, 424/9.321, 9.51, 417; 264/4.1, 4.3; 428/402.2

(56) References Cited

U.S. PATENT DOCUMENTS 5,085,864 A * 2/1992 Cannon ...................... 424/450

FOREIGN PATENT DOCUMENTS

| EP | 0056781 | * | 7/1982 |
| EP | 0133258 | | 7/1984 |
| EP | 0315467 | | 5/1989 |
| EP | 0453525 | | 10/1990 |
| EP | 0475160 | * | 3/1992 |
| WO | 8807855 | | 10/1988 |
| WO | 9401089 | * | 1/1994 |

OTHER PUBLICATIONS

Weder, Liposome Technology, Chap. 7.*
Lichtenberg, Methods of Biochemical Analysis. 1988.*

* cited by examiner

Primary Examiner—Gollamudi S. Kishore
(74) Attorney, Agent, or Firm—Finnegan, Henderson, Farabow, Garrett and Dunner LLP

(57) ABSTRACT

An aqueous liposome system comprises at least one phospholipid, a non-phospholipidic substance which is a bile acid or derivative thereof, and, optionally, a non-toxic organic solvent. The mass ratio of phospholipid to the non-phospholidic substance is in the range between 1:0.001 and 1:0.1. The diameter of the liposomes formed in this liposome system is in the range between 35 and 90 nm. The liposome system is stable over large periods of time, e.g., several months or years, and is highly transparent. The liposomes may be loaded with a pharmaceutically active ingredient.

12 Claims, No Drawings

AQUEOUS LIPOSOME SYSTEM AND A METHOD FOR THE PREPARATION OF SUCH A LIPOSOME SYSTEM

This is a continuation of application Ser. No. 08/459,291, now abandoned, filed Jun. 2, 1995, which is a continuation of application Ser. No. 08/205,520, filed Mar. 3, 1994, now abandoned.

The present invention relates to an aqueous liposome system with the characteristic features of the preamble of claim 1 and a method for the preparation of such a liposome system.

Different use are known for aqueous liposome systems. Such systems may for instance be used in cosmetics or for the preparation of pharmaceutical products. They are characterised by the fact that they contain hollow vesicles, also known as liposomes, which have an inner sphere containing an aqueous phase. Depending on the respective use the aqueous phase in the inner part of the hollow vesicles may contain a pharmaceutically or cosmetically active ingredient in a dissolved, a dispersed or a suspended form. The system described by EP-A 0 315 457 is an example of such a liposome system whereby these liposome systems contain the drug pentamidine in the inner part of the vesicles.

Furthermore aqueous liposome systems are known, which contain in the inner part of the vesicles only the aqueous phase, such liposome systems being called an unloaded liposome system which can, if needed, be loaded subsequently with a pharmaceutically or cosmetically active product.

Both types of the above-described aqueous liposome systems have as a barrier to the outer phase a lipid double membrane.

The liposome systems known from the prior art have a frequent disadvantage, that they show the tendency to form unwanted sediments after a short time.

The object of the subject invention is to provide an aqueous liposome system which comprises besides a non-toxic organic solvent at least one phospholipid, which possesses a particularly high stability and does not lead to unwanted sedimentation.

The inventive aqueous liposome system which comprises optionally besides a non-toxic organic solvent at least one phospholipid, comprises besides said phospholipid constituting the liposome system a further substance, which is not a phospholipid. This further non-phospholipidic substance is a bile acid, a bile acid salt, a bile acid derivative and/or a salt of a bile acid derivative, the mass ratio between said phospholipid and said further non-phospholipidic substance varying between 1:0.001 and 1:0.1.

The inventive liposome system has a number of advantages. So, it could be observed, that the inventive liposome system even at a storage period of several months or years did not show any tendency to form sediments or deposits on the inner walls of the vessels. Furthermore, the inventive liposome system has a high transparency and does not show any opalescence as do the liposome systems known in the art. Due to the lack of sedimentation and deposit formation and the high transparency the inventive liposome system can be inspected quite easily on the presence of foreign particles, since such an inspection may be simply performed by looking through the same.

The above advantageous properties of the inventive liposome system are thought to depend on a synergistic effect brought about by the presence of the small amounts of the further non-phospholipidic substance (a bile acid, a bile acid salt, a bile acid derivative and/or a salt of a bile acid derivative), which is not present in natural phospholipid systems.

Particularly good properties in respect to the before-mentioned advantages are shown by a first embodiment of the inventive aqueous liposome system, in which the mass ratio of the phospholipid to the further non-phospholipidic substance (a bile acid, a bile acid salt, a bile acid derivative and/or a salt of a bile acid derivative) is between 1:0.03 and 1:0.1.

As mentioned before, the inventive phospholipid preparation comprises at least one further non-phospholipidic substance. This concerns in particular a salt, in particular a sodium and/or an ammonium salt, of cholic acid, deoxycholic acid, ursodeoxycholic acid and/or chenodeoxycholic acid but may also be the salt, in particular a sodium and/or an ammonium salt, of a bile acid derivative, preferably glycocholic acid and/or taurocholic acid.

A further particularly suitable embodiment of the inventive liposome system provides, that the inventive liposome system contains as the further non-phospholipidic substance glycocholic acid, a salt of glycocholic acid and/or a derivative of glycocholic acid within the previously mentioned range of mass ratios.

The concentration of the at least one phospholipid varies between 5% by weight and 25% by weight, in particular between 8% by weight and 18% by weight, these concentration values relating to the final liposome system or to a liposome system as is offered commercially. It is obvious, that depending on the respective intended type of treatment or the intended case to be treated, higher as well as lower phospholipid concentrations as the above values are possible.

A particularly high stability and a particularly homogeneous distribution of the liposomes with respect to their diameter is found at another embodiment of the inventive liposome system, when it contains phosphatidylcholine, in particular such a phosphatidylcholine (3-sn-phosphatidylcholine, soya) which is gained from soybean. In particular in cases where the phospholipid in the inventive liposome system constitutes to at least 90% by weight and preferably to at least 95% by weight of phosphatidylcholine, then such a liposome system possesses the advantages which were mentioned previously in even more pronounced form. Additionally, such a special liposome system can with essentially less effort and for that reason in about half of the usual time be reduced in a homogeneous way by extrusion, high pressure split homogenisation or ultrasound treatment to a wanted mean particle diameter of between 30 and 100 nm, in particular of between 35 and 90 nm. Also such a special liposome system which contains mostly unilamellar to bilamellar liposomes of the said dimension, to be filtrated easily, whereby preferably 0.2 $\mu$m filters are being used.

A further advantage of the inventive liposome system is the fact, that it possesses a pH value which varies around neutrality and lies preferably between 6.0 and 8.0 and more preferably between 6.2 and 7.4.

As stated previously, the inventive liposome system comprises mostly unilamellar or bilamellar liposomes with a particle diameter between 30 nm and 100 nm, preferably between 35 nm and 90 nm.

The inventive liposome system can be used for pharmaceutical as well as cosmetic purposes, this use covering the unloaded liposomes as well as such liposome systems loaded with a respective pharmaceutically or cosmetically active ingredient.

If the inventive liposome system was used in the form of an unloaded liposome system without any encapsulated active ingredient, it could be observed that said unloaded system is perfectly suited for the treatment of atherosclerosis, increased blood lipid values as well as the treatment of liver diseases of any type. Said unloaded liposome system comprises preferably besides water and eventually an alcohol between 5% by weight and 20% by weight of a mixture of phosphatidylcholine of the beforementioned purity and the further non-phospholipidic substance (bile acid, a bile acid salt, a bile acid derivative and/or a salt of a bile acid derivative of the afore-mentioned type) in the mass ratio as mentioned previously. Such a pharmaceutical product is particularly suitable for injection.

As has been mentioned before, the inventive liposome system may contain an encapsulated cosmetic or pharmaceutical active ingredient. It has been observed, that such an encapsulated active ingredient has a greater therapeutic efficacy in particular with respect to its duration, in comparison with conventional application form, like e.g. a tablet, a sugar-coated tablet or the like. This greater efficacy enables as a rule the reduction of the amount of the active ingredient, without this having a negative effect on the therapeutic efficacy. This depot effect may be explained by a regular and long-lasting release of the encapsulated active ingredient from the liposome system. As a result any unwanted side effects do not appear, or at least in a less severe form. The selection of the active ingredient depends on the type of treatment. It is possible to encapsulate in the inventive liposome system pentamidine, pentamidine salts, in particular pentamidine isethionate and/or pentamidine derivatives dissolved and/or encapsulated, such a pharmaceutical product then preferably being used for the parenteral and in particular for the pulmonary treatment of *Pneumocystis carinii* Pneumonia, the African sleeping disease or of Kala-Azar.

It is particularly suitable, not to use the pharmaceutical or cosmetic active ingredient from the beginning in the preparation of the liposome system, but to add said pharmaceutically or cosmetically active ingredient only after the preparation of the liposome system and in particular immediately before use. For example, this can be obtained, by mixing an aqueous unloaded liposome system with the active ingredient, whereby this active ingredient is present in dry form, or as a solution, dispersion, emulsion or suspension in a non-toxic organic solvent, or by dispersing a dried liposome system in water in which the active ingredient has been dissolved. Pharmaceutical or cosmetic products prepared in this way show a high transparency, which makes it an easy task to inspect them on the presence of unwanted foreign particles.

If the inventive liposome system comprises as active ingredient doxorubicin hydrochloride, then such a product may be used for the treatment of cancer disease.

If on the other hand, the inventive liposome system is to be used for the treatment of viral diseases, in particular of viral skin diseases, then the active ingredient to be encapsulated in the vesicles will be an virucidal agent, like e.g. rosmarinic acid or dextrane sulphate.

Furthermore the known active ingredients for the treatment of cancer, Aids, liver disease or virus disease can also be encapsulated.

The invention further relates to a method for the production of the above-described liposome system.

According to the inventive method for producing the liposome system initially the at least one phospholipid is dissolved or dispersed in an organic solvent together with the at least one further non-phospholipidic substance, which may be a bile acid, a bile acid salt, a bile acid derivative and/or a salt of a bile acid derivative, the mass ratio being 1:0.001 to 0.01, preferably 1:0.3 to 1:0.1.

Subsequently this solvent is partially or completely evaporated from the solution or dispersion and the liposome system is then formed by the addition of water.

The inventive method provides a number of advantages. Surprisingly it was observed, that the inventive method makes is possible to produce in a particularly simple, rapid and cheap manner aqueous liposome systems which possess a pronounced storage stability, which do not lead to sedimentation, which do not lead to formation of deposits on the inner vessel walls and which show in addition a large transparency, allowing a particularly simple and rapid inspection on foreign particles. Furthermore the liposome system produced according to the inventive method shows highly reproducible particle sizes, in particular such unilamellar or bilamellar liposomes being produced, with particle diameters varying between 30 and 100 nm, preferably between 35 and 90 nm. It is also possible, to perform sterile filtration of the liposome system produced according to the inventive method, where the use of a 0.2 $\mu$m filter is being preferred.

The organic solvent used for dissolving the at least one phospholipid and the further non-phospholipidic substance is a non-toxic solvent in which both the phospholipid and the non-phospholipidic substance (bile acid, a bile acid salt, a bile acid derivative and/or a salt of a bile acid derivative) can be dissolved. It is preferred to use as organic solvent ethanol, 1-propanol, 2-propanol or benzyl alcohol.

Depending on the type of non-toxic organic solvent used and its mixing properties with water, the solvent is partially or completely evaporated from the solution or dispersion initially prepared according to the inventive method to different final amounts of the organic solvent. These final amounts may vary between 0 volume % and 20 volume %, preferably between 0 volume % and 10 volume %. When the organic solvent used according to the inventive method is not water-miscible, then the organic solvent is removed to dryness.

If in the inventive method the reproducibility of the particle size of the liposome system should be further improved, so that in the liposome system which is produced by the inventive method the range of particle sizes is small, it is recommended to subject the liposome system, comprising the at least one phospholipid and the further non-phospholipidic substance (a bile acid, a bile acid salt, a bile acid derivative and/or a salt of a bile acid derivative) to an extrusion, a high pressure homogenisation and/or an ultrasound treatment. Preferably this treatment is performed at a temperature below 40° C., in particular at a temperature between 20° C. and 30° C.

The duration of the extrusion, the high pressure split homogenisation or the ultrasound treatment is chosen to be sufficiently long for the liposomes to show the wanted mean diameter. Said extrusion, high pressure split homogenisation or ultrasound treatment is performed until the liposomes formed possess a mean diameter of between 30 nm and 100 nm, preferably between 35 nm and 90 nm.

A further embodiment of the inventive method is the sterile filtration of the liposome system produced according to the inventive method, preferably with a 0.2 $\mu$m filter.

The liposome systems produced according to the inventive method can be filled directly in corresponding ampoules in a condition ready for use. According to a particularly suitable embodiment of the inventive method the liposome system which is formed after the addition of water is dried carefully after the addition of a suitable additive in particular a carbohydrate, whereby lyophilisation constitutes the best method for this careful drying. According to this embodiment of the inventive method a powder-like liposome system is obtained, which can be reverted into the vesicles by the addition of a suitable amount of water. It is not necessary to subject the liposome system formed after the addition of water to extensive agitation or for instance to high pressure split homogenisation or ultrasound treatment.

As has been explained before, it is preferred to use in the inventive method a soybean phospholipid and in particular such a soybean phospholipid which contains a large concentration of phosphatidylcholine, preferably at least 90% by weight phosphatidylcholine.

Two possibilities exist to produce the liposome system according to the inventive method comprising the above-mentioned pharmaceutically or cosmetically active ingredient.

According to the first possibility, the active ingredient is added together with the phospholipid and the further non-phospholipidic substance (a bile acid, a bile acid salt, a bile acid derivative and/or a salt of a bile acid derivative) in the above-mentioned mass ratio to the organic solvent used.

According to a variant of this method, a phospholipid is used which is loaded with the active ingredient. For this purpose the selected phospholipid is soaked with the non-aqueous solution, dispersion or suspension containing the active ingredient and subsequently performing a careful drying of the phospholipid loaded with the active ingredient in this manner. Thereafter the phospholipid loaded with the active ingredient dissolved together with the further substance which is not a phospholipid in an organic solvent, which may optionally be a different one from solvent used for the loading step. Hereafter the organic solvent is removed completely or partially as was described above at the description of the inventive method, and when in the final step the water is added a liposome system with an encapsulated active ingredient is formed. This variant of the inventive method is especially recommendable in cases where the active ingredient shows a good storage stability.

According to the second possibility which is to be preferred when the active ingredient is better soluble in water than in the organic solvent, the at least one phospholipid is dissolved or dispersed initially together with the at least one non-phospholipidic substance in the selected organic solvent. After the removal of the solvent from the solution or the dispersion the active ingredient is added together with the water, whereby it is preferred to dissolve the active ingredient in the water.

A modification of the above-described variant of the method, which is used especially when the active ingredient has a limited stability, is based on a powder-like dried liposome system. During the redispersion step the active ingredient is added together with the amount of water, so that the active ingredient is encapsulated into contact with liposome system only immediately prior to the use of such a product and is therefore protected against ageing.

To prevent unwanted side effects, the inventive method is performed under protection gas (inert gas).

As has been mentioned before at the description of the inventive aqueous liposome system, the preferred phospholipid concentration lies between 5% by weight and 25% by weight, in particular between 8% by weight and 18% by weight, whereby, depending on the intended use and the type of treatment, these concentration values may be higher and lower, as long as the mass ratio of phospholipid to the further non-phospholipidic substance is within the range given before. Accordingly a required amount of phospholipid is selected and the mass ratio of phospholipid to the at least one non-phospholipidic substance is chosen according to the defined range (1:0.001 to 1:0.1).

The following examples are further illustrations of the inventive method.

For the preparation of several aqueous liposome systems, the following compositions I to VIII are dissolved in 500 ml ethanol. Subsequently the solvent is removed under vacuum to dryness. The residue was dispersed in 1000 ml water and brought thereafter by high pressure split homogenisation to a mean particle diameter between 30 nm and 100 nm. Hereafter the obtained liposome system was filtrated under sterile conditions through a 0.2 μm filter and filled under sterile conditions into ampoules.

To prevent unwanted oxidation reactions the preparative method was performed under inert gas (nitrogen).

The following compositions I to VIII were used according to the previously mentioned procedure, the indicated phosphatidylcholine being a highly pure soybean phosphatidylcholine (3-sn-phosphatidylcholine, soya), which contained at least 90% by weight phosphatidylcholine.

Composition I
  100 g phosphatidylcholine
Composition II
  99.5 g phosphatidylcholine
  0.5 deoxycholic acid sodium salt
Composition III
  99.5 g phosphatidylcholine
  0.5 g chenodeoxycholic acid sodium salt
Composition IV
  99.5 g phosphatidylcholine
  0.5 g cholic acid sodium salt
Composition V
  95 g phosphatidylcholine
  5 g glycocholic acid sodium salt
Composition VI
  99 g phosphatidylcholine
  1 g glycocholic acid sodium salt
Composition VII
  99.5 g phosphatidylcholine
  0.5 g glycocholic acid sodium salt
Composition VIII
  99.7 g phosphatidylcholine
  0.3 g glycocholic acid sodium salt The aqueous liposome system of composition I had strongly differing properties from the compositions II to VIII as can be taken from the following table 1

TABLE 1

| composition | appearance | mean particle size (nm) | transparency in % (660 nm) | pH |
|---|---|---|---|---|
| I | opalescent emulsion | 123 | ca 1 | 6.0 |
| II | yellowish transparent fluid | 48 | 89 | 6.1 |
| III | yellowish transparent fluid | 42 | 90 | 7.4 |
| IV | yellowish transparent fluid | 44 | 91 | 7.2 |
| V | yellowish transparent fluid | 44 | 96 | 7.2 |
| VI | yellowish transparent fluid | 40 | 94 | 6.5 |

TABLE 1-continued

| composition | appearance | mean particle size (nm) | transparency in % (660 nm) | pH |
|---|---|---|---|---|
| VII | yellowish transparent fluid | 45 | 92 | 6.2 |
| VIII | yellowish transparent fluid | 45 | 89 | 6.2 |

The aqueous liposome systems II to VIII could easily and with a large yield be filtrated in a sterile manner through a 0.2 μm filter whereas filtration of the aqueous liposome system from composition I was not possible.

What is claimed is:

1. An aqueous liposome system comprising at least one phospholipid, a non-phospholipidic substance selected from the group consisting of cholic acid, deoxycholic acid, ursodeoxycholic acid, chenodeoxycholic acid, glycocholic acid, taurocholic acid, and their respective sodium and ammonium salts, and, optionally, a non-toxic organic solvent, the mass ratio of said phospholipid to said non-phospholipidic substance being in the range between 1:0.001 and 1:0.1, wherein the diameter of liposomes in said liposome system is in the range between 35 and 90 nm.

2. The liposome system of claim 1 wherein the mass ratio of said phospholipid to said non-phospholipid substance is in the range between 1:0.03 and 1:0.1.

3. The liposome system of claim 1 wherein said non-phospholipidic substance is glycocholic acid.

4. The liposome system of claim 1 wherein the phospholipid is present in a concentration between 5% and 25% by weight of said liposome system.

5. The liposome system of claim 1 wherein the phospholipid is present in a concentration between 8% and 18% by weight of said liposome system.

6. The liposome system of claim 1 wherein said phospholipid is predominantly phosphatidylcholine.

7. The liposome system of claim 1 wherein said phospholipid comprises at least 90% by weight phosphatidylcholine.

8. The liposome system of claim 1 wherein said phospholipid is a soybean phospholipid.

9. The liposome system of claim 1 wherein said liposome system has a pH between 6.0 and 8.0.

10. The liposome system of claim 1 further comprising at least one pharmaceutically active ingredient.

11. The liposome system of claim 10 wherein said pharmaceutically active ingredient comprises a drug for the treatment of cancer, liver disease, viral disease or *Pneumocystis carinii* pneumonia.

12. The liposome system of claim 11 wherein said viral disease is AIDS.

* * * * *

UNITED STATES PATENT AND TRADEMARK OFFICE
CERTIFICATE OF CORRECTION

PATENT NO. : 6,663,885 B1 Page 1 of 1
DATED : December 16, 2003
INVENTOR(S) : Hager et al.

It is certified that error appears in the above-identified patent and that said Letters Patent is hereby corrected as shown below:

<u>Title page,</u>
Item [*] Notice, delete "2059 days" and replace with -- 1826 days --.

Signed and Sealed this

Thirteenth Day of June, 2006

JON W. DUDAS
*Director of the United States Patent and Trademark Office*